United States Patent
Bös et al.

(10) Patent No.: US 6,552,088 B2
(45) Date of Patent: Apr. 22, 2003

(54) BIPHENYL DERIVATIVES

(75) Inventors: Michael Bös, Montreal (CA); Guido Galley, Rheinfelden (DE); Thierry Godel, Basel (CH); Torsten Hoffmann, Birsfelden (CH); Walter Hunkeler, Magden (CH); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/886,669

(22) Filed: Jun. 21, 2001

(65) Prior Publication Data

US 2002/0040060 A1 Apr. 4, 2002

Related U.S. Application Data

(62) Division of application No. 09/513,147, filed on Feb. 25, 2000.

(30) Foreign Application Priority Data

Mar. 9, 1999 (EP) .............................. 99104626

(51) Int. Cl.⁷ ................... C07C 233/00; C07D 241/04; A61K 31/495; A61K 31/165
(52) U.S. Cl. ....................... 514/647; 514/716; 514/717; 568/659; 568/583; 568/660; 568/661; 564/307; 564/308; 564/309
(58) Field of Search .................. 568/659, 583, 568/660, 661; 564/307, 308, 309; 514/647, 716, 717

(56) References Cited

U.S. PATENT DOCUMENTS 5,972,938 A  10/1999  Rupniak et al.

FOREIGN PATENT DOCUMENTS

| WO | WO 95/16679 | 6/1995 |
| WO | WO 95/18124 | 7/1995 |
| WO | WO 95/23798 | 9/1995 |
| WO | WO 98/47875 | 10/1998 |

OTHER PUBLICATIONS

Barker, R., *Reviews in the Neurosciences*, vol. 7, pp. 187–214 (1996).
Longmore, J. et al, *Canadian J. Physiol. Pharmacol.*, vol. 75, pp. 612–621 (1997).
Kramer, M. et al, *Science*, vol. 281, pp. 1640–145 (1998).
Maggi, C. et al, *J. Auton. Pharmacol*, vol. 13, pp. 23–93 (1993).
Navari, R. et al, *New England J. of Medicine*, vol. 340, No. 3, pp. 190–195 (1999).
STN Information System File: Registry, XP002140608.
STN Information System File: Registry, XP002140609.

*Primary Examiner*—Richard L. Raymond
*Assistant Examiner*—Hong Liu
(74) *Attorney, Agent, or Firm*—George W. Johnston; Patricia S. Rocha-Tramaloni

(57) ABSTRACT

Biphenyl substituted amides with activity as antagonists of the neurokinin 1 (NK-1, substance P) receptor.

4 Claims, No Drawings

BIPHENYL DERIVATIVES

This application is a division of U.S. patent application Ser. No. 09/513,147, filed on Feb. 25, 2000.

BACKGROUND OF THE INVENTION

The neuropeptide receptors for Neurokinin 1 (substance P, NK-1) are widely distributed throughout the mammalian nervous system (especially brain and spinal ganglia), the circulatory system and peripheral tissues (especially the duodenum and jejunum) and are involved in regulating a number of diverse biological processes. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The central and peripheral actions of the mammalian tachykinin, substance P, have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (*Neurosci. Res.*, 1996, 7, 187–214) anxiety (*Can. J. Phys.*, 1997, 75, 612–621) and depression (*Science*, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases is reviewed in "Tachykinin Receptor and Tachykinin Receptor Antagonists", *J. Auton. Pharmacol.*, 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1-receptor antagonists are further useful for the treatment of motion sickness and for treament induced vomiting.

In addition, in The New England Journal of Medicine, Vol. 340, No.3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

SUMMARY OF THE INVENTION

In accordance with the present invention, the compounds of formula I and their salts are characterized by valuable therapeutic properties. It has been surprisingly found that the compounds of the present invention are antagonists of the Neurokinin 1 (NK-1, substance P) receptor.

Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION OF THE INVENTION

The present invention relates to compounds of the formula:

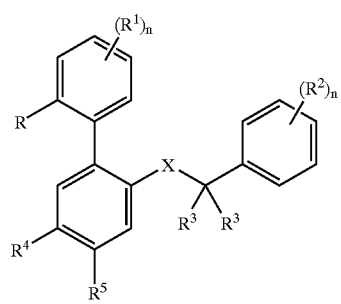

wherein
R is hydrogen, lower alkyl, lower alkoxy, halogen, amino, —N(R$^6$)$_2$ or trifluoromethyl;
R$^1$ is hydrogen, lower alkoxy or halogen;
R and R$^1$ may be together —CH=CH—CH=CH—;
R$^2$ is halogen, lower alkyl or trifluoromethyl;
R$^3$ is hydrogen or lower alkyl;
R$^4$ is hydrogen or a cyclic tertiary amine, optionally substituted by lower alkyl;
R$^5$ is hydrogen, nitro, amino or —N(R$^6$)$_2$;
R$^6$ is hydrogen or lower alkyl;
X is —C(O)N(R$^6$)—, —(CH$_2$)$_n$O—, —(CH$_2$)$_n$N(R$^6$)—, —N(R$^6$)C(O)— or —N(R$^6$)(CH$_2$)$_n$—; and
n is 1–2;
and to pharmaceutically acceptable acid addition salts thereof.

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3–6 carbon atoms.

The term "cyclic tertiary amine" denotes, for example, pyrrol-1-yl, imidazol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl. Preferred is the piperazine group.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred are compounds, in which X is —C(O)N($R^6$)—, wherein $R^6$ is methyl, for example the following compounds:

2'-methyl-biphenyl-2-carboxylic acid-(3,5-bis-trifluoromethyl-benzyl)-methyl-amide, 2'-methyl-5-(4-methyl-piperazin-1-yl)-biphenyl-2-carboxylic acid-(3,5-bis-trifluoromethyl-benzyl)-methyl-amide and 2'-chloro-5-(4-methyl-piperazin-1-yl)-biphenyl-2-carboxylic acid-(3,5-bis-trifluoromethyl-benzyl)-methyl-amide.

Further preferred are compounds, in which X is —N($R^6$)—CO—, wherein $R^6$ is methyl.

Examples of such compounds are:

2-(3,5-bis-trifluoromethyl-phenyl)-N-methyl-N-(2'-methyl-4-nitro-biphenyl-2-yl)-isobutyramide, N-(4-amino-2'-methyl-biphenyl-2-yl)-2-(3,5-bis-trifluoromethyl-phenyl)-N-methyl-isobutyramide, 2-(3,5-bis-trifluoromethyl-phenyl)-N-methyl-N-(2'-methyl-4-methylamino-biphenyl-2-yl)-isobutyramide, 2-(3,5-bis-trifluoromethyl-phenyl)-N-methyl-N-(2'-methyl-biphenyl-2-yl)-isobutyramide and N-(2'-amino-biphenyl-2-yl)-2-(3,5-bis-trifluoromethyl-phenyl)-N-methyl-isobutyramide.

The present compounds of formula I and their pharmaceutically acceptable salts can be prepared by methods known in the art, for example, by processes described below, which process comprises a) reacting a compound of formula:

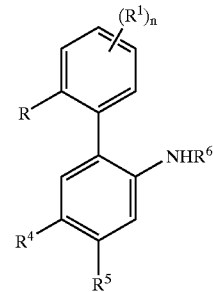

with a compound of formula:

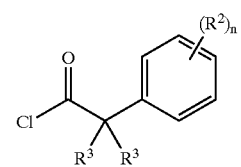

to a compound of formula:

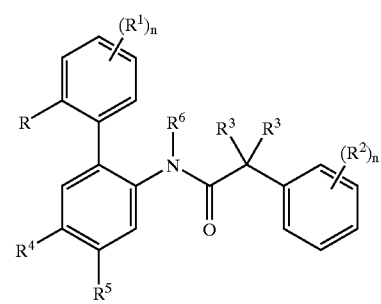

wherein $R^1$–$R^6$, R and n have the significances given above, or b) reacting a compound of formula:

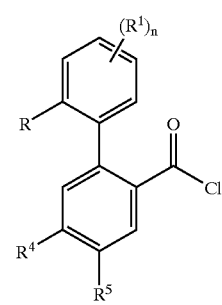

with a compound of formula:

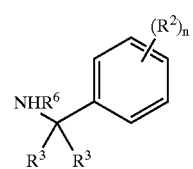

to give a compound of formula:

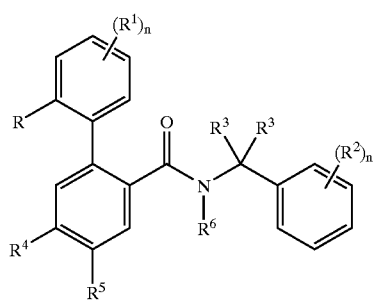

I-2 wherein $R^1$–$R^6$, R and n have the significances given above, or c) reducing a compound of formula:

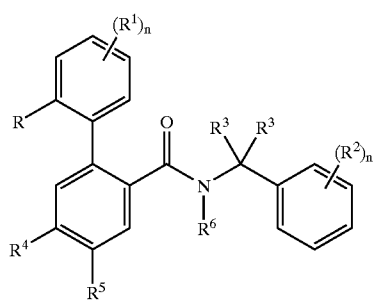

I-2 to a compound of formula:

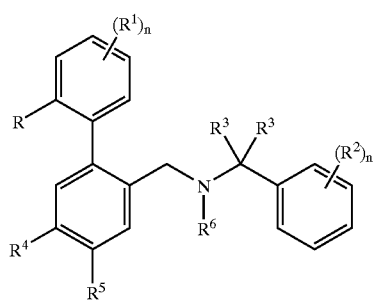

I-4 wherein the definitions of substituents are given above, or d) reacting a compound of formula:

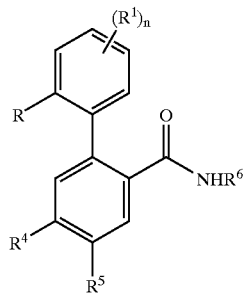

VI with a compound of formula:

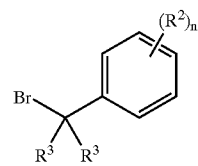

VII to a compound of formula:

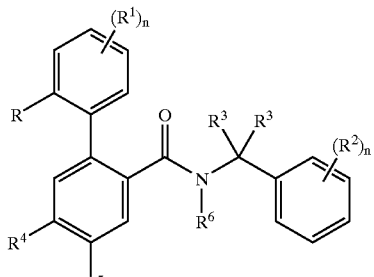

I-2 wherein the definitions of substituents are given above, or e) reacting a compound of formula:

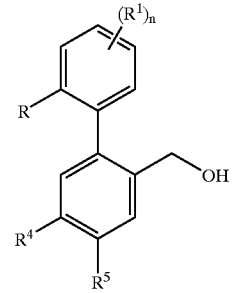

VIII with a compound of formula:

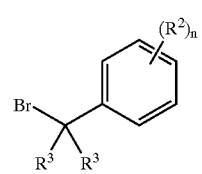

VII to a compound of formula:

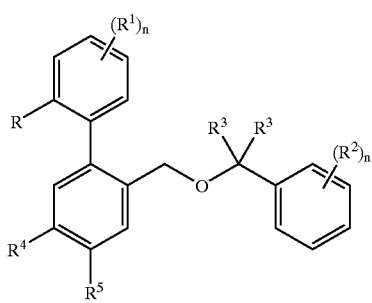

I-5 wherein the definitions of substituents are given above, or i) reducing a compound of formula:

I-1

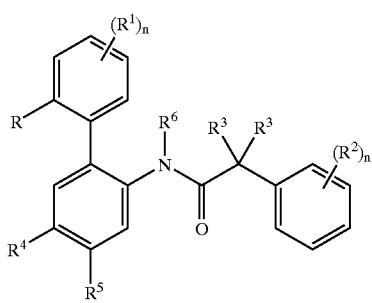

to a compound of formula:

I-3 wherein the definitions of substituents are given above, or g) reacting a compound of formula:

XII

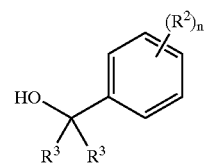

with a compound of formula:

XIII

HO—C(R³)(R³)—Ar(R²)ₙ to a compound of formula:

I-5 wherein the definitions of substituents are given above, or h) methylating a compound of formula:

I-41 to a compound of formula:

I-42 wherein the substituents are given above, or i) reacting a compound of formula:

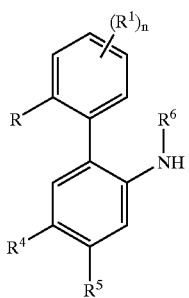

II with a compound of formula:

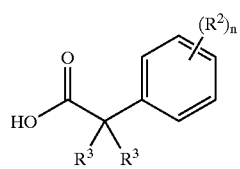

XIII to a compound of formula:

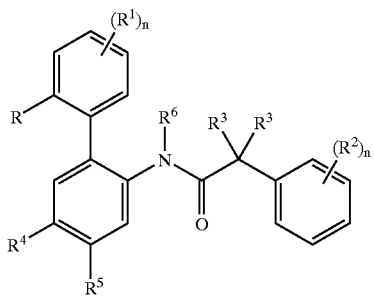

I-1 wherein the definition of substituents is given above, or j) modifying one or more substituents $R^1$–$R^6$ or R within the definitions given above, and if desired, converting the compound obtained into a pharmaceutically acceptable acid addition salt.

In accordance with process variant a) to a cooled solution of a compound of formula II, for example 2'-methyl-4-nitro-biphenyl-2-amine and DIPEA (N-ethyldiisopropyl-amine) is added a solution of a compound of formula III, for example 2-(3,5-bis-trifluoromethyl-phenyl)-2-methyl-propionyl chloride in dichloromethane and the mixture is stirred at temperatures between 35–40° C. The desired compound of formula I-1 is yielded after purification in good yields.

Process variant b) describes the reaction of a compound of formula IV with a compound of formula V to a compound of formula I-2. The reaction is carried out in conventional manner, for example in a solvent, such as toluene and in presence of triethyl-amine. The mixture is refluxed for about 1 hour.

In accordance with process variant c) a compound of formula I-2 is reduced to a compound of formula I-4. This reaction is carried out with a reducing agent, such as $LiAlH_4$ or $BH_3$.THF, in conventional manner.

Process variant d) describes the reaction of a compound of formula VI with a compound of formula VII to a compound of formula I-2. This reaction is carried out by deprotonation of a compound of formula VI with KHMDS (potassium hexamethyldisilazide) and subsequent addition of a compound of formula VII. A suitable solvent is tetrahydrofuran. The reaction is carried out at room temperature.

In accordance with process variant e) a compound of formula I-5 is prepared. This reaction is carried out by deprotonation of a compound of formula VIII with NaH and subsequent addition of a compound of formula VII. This reaction is carried out in conventional manner.

A further method for the preparation of a compound of formula I is described in process variant f). A compound of formula I-1 is reduced to a compound of formula I-3 in conventional manner, for example with $LiAlH_4$ or $BH_3$.THF.

In accordance with variant g) a compound of formula XII is reacting with a compound of formula XIII to give a compound of formula I-5. This reaction is carried out in conventional manner with NaH in the presence of a solvent, such as DMF.

Reaction variant h) describes the methylation of a compound of formula I-41 with formaline and $NaBH_4$ to a compound of formula I-42.

Process variant i) describes the process for preparation of a compound of formula I-1, wherein a compound of formula XIII is activating with CDI and subsequent addition of a compound of formula II yields a compound of formula I-1.

The salt formation is effected at room temperature in accordance with methods which are known per se and which are familiar to any person skilled in the art. Not only salts with inorganic acids, but also salts with organic acids came into consideration. Hydrochlorides, hydrobromides, sulphates, nitrates, citrates, acetates, maleates, succinates, methan-sulphonates, p-toluenesulphonates and the like are examples of such salts.

The following schemes 1–5 describe the processes for preparation of compounds of formula I in more detail. The starting materials of formulae II, III, IX, X, XI, XII, XIII, XIV and XV are known compounds and may be prepared according to methods known in the art.

In the schemes the following abbreviations have been used:

| | |
|---|---|
| EDCI | N-(3-dimethylaminopropyl)-N'-ethylcarbodiimide hydrochloride |
| HOBT | 1-hydroxybenzo-triazole |
| DMF | dimethylformamide |
| CDI | 1,1'carbonyldiimidazoletetrahydrofuran |
| TMEDA | N,N,N',N'-tetramethylethylene diamine |
| KHMDS | potassium hexamethyldisilazide |
| $NaBH_4$ | sodiumborohydride |
| $NaCNBH_4$ | sodiumcyanoborohydride |
| TFA | trifluoroacetic acid |
| DIEA | N,N-diisopropylethylamin |

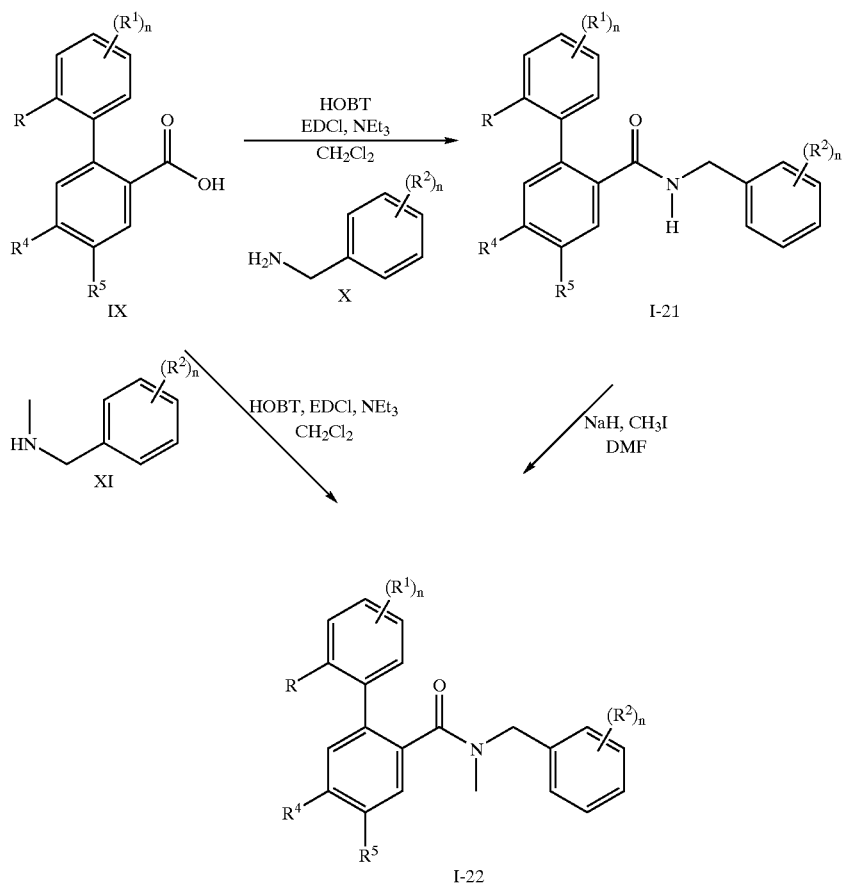
The substituents are given above.
The definition of substituents is given above.

Scheme 3
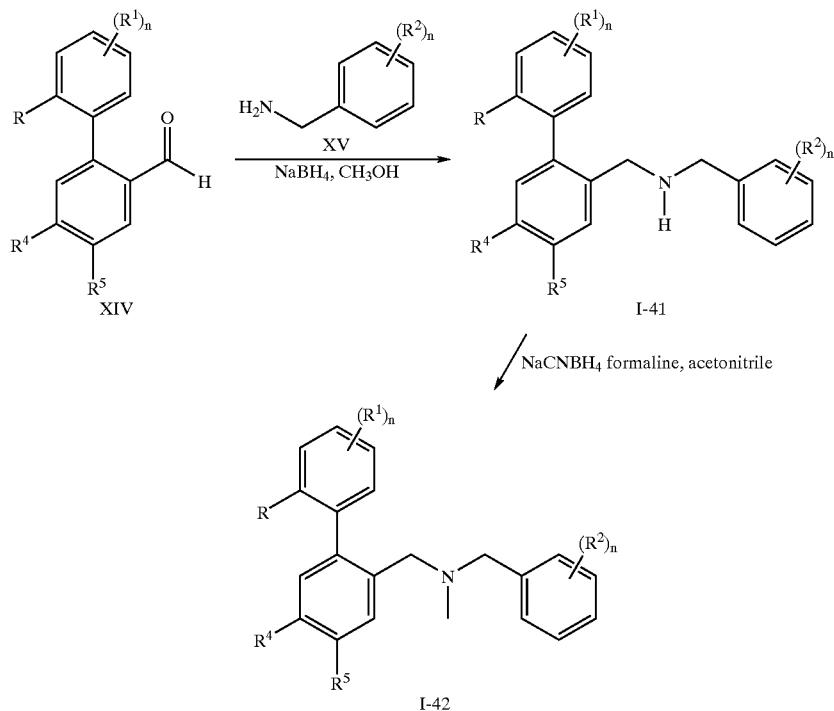
The definition of substituents is given above.
Scheme 4
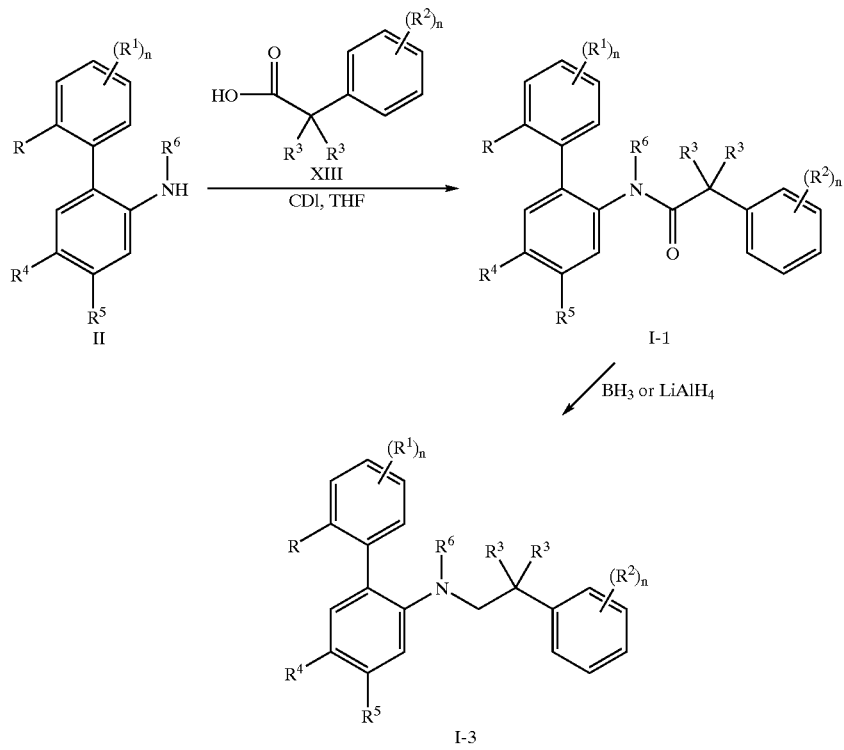

The definition of substituents is given above.
Scheme 5
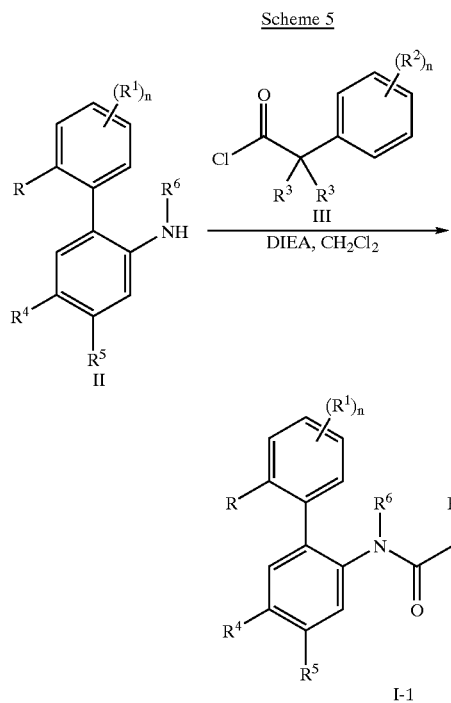
The definition of substituents is given above.
Scheme 7
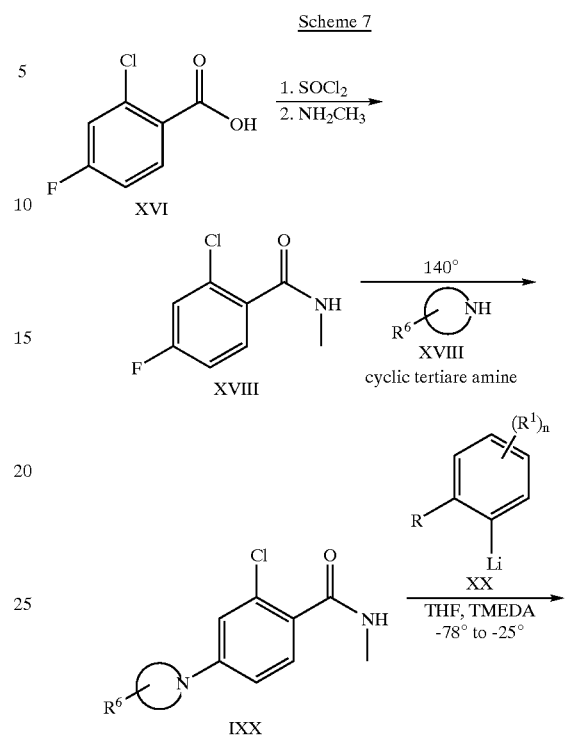
Scheme 6
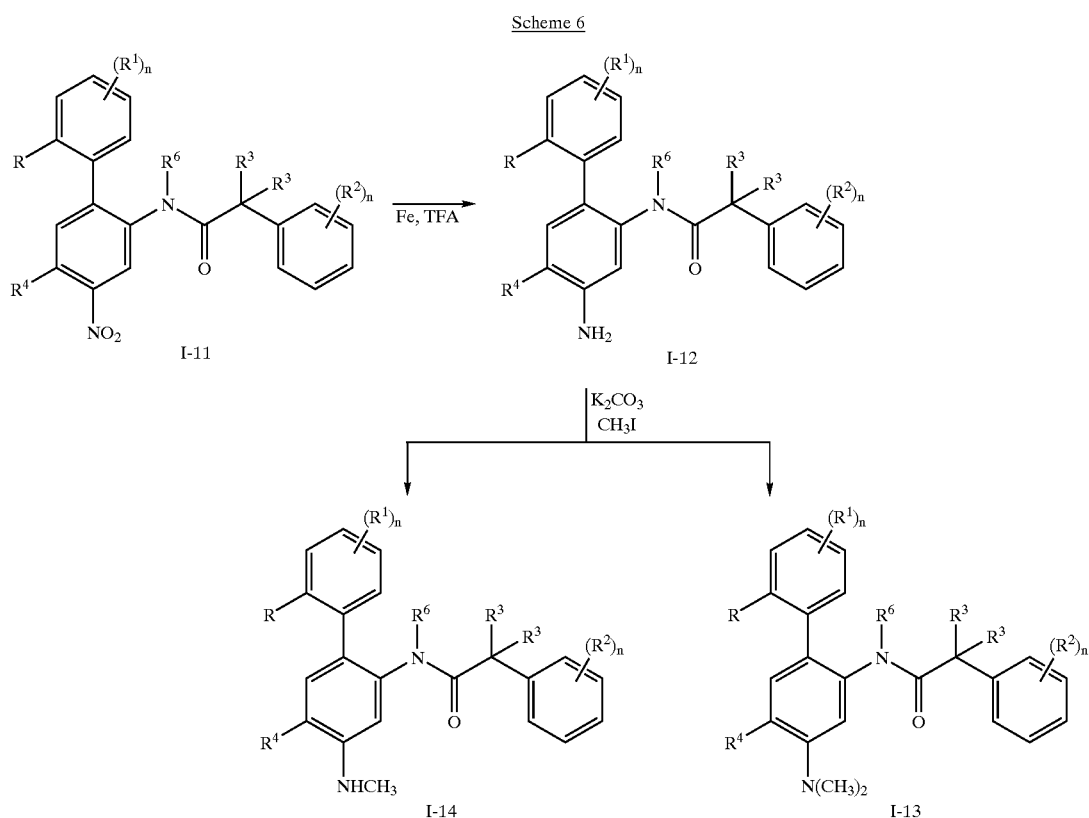

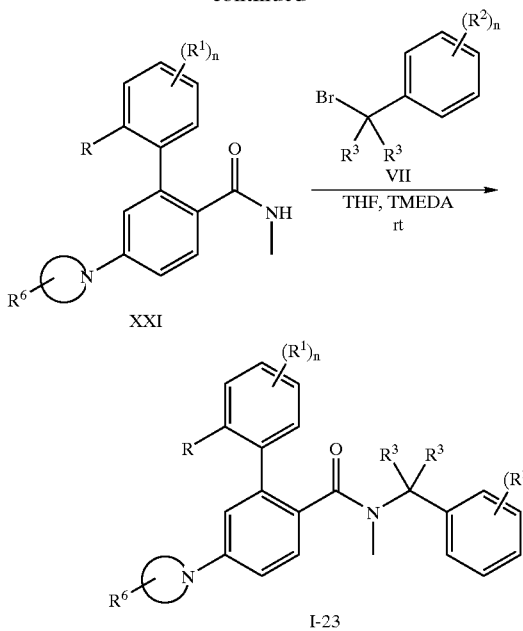

The definition of substituents is given above.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the NK-1 receptor was evaluated at human NK-1 receptors in CHO cells infected with the human NK-1 receptor (using the Semliki virus expression system) and radiolabelled with [3H] substance P (final concentration 0.6 nM). Binding assays were performed in HEPES buffer (50 mM, pH 7.4) containing BSA (0.04%) leupeptin (8 μg/ml), MnCl$_2$ (3 mM) and phosphoramidon (2 μM). Binding assays consisted of 250 μl of membrane suspension (1.25×105 cells/assay tube), 0.125 μl of buffer of displacing agent and 125 μl of [3H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washed of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 8.00–9.00 for the preferred compounds. Examples of such compounds are:

| | |
|---|---|
| N-(4-amino-2'-methyl-biphenyl-2-yl)-2-(3,5-bis-trifluoromethyl-phenyl)-N-methyl-isobutyramide | 8.28 |
| 2-(3,5-bis-trifluoromethyl-phenyl)-N-methyl-N-(2'-methyl-4-methylamino-biphenyl-2-yl)-isobutyramide | 8.01 |
| 2'-methyl-5-(4-methyl-piperazin-1-yl)-biphenyl-2-carboxylic acid(3,5-bis-trifluoromethyl-benzyl)-methyl-amide | 8.84 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragées and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. All temperatures are given in degrees Celsius.

EXAMPLE 1

Biphenyl-2-carboxylic acid (3,5-bis-trifluoromethyl-benzyl)-methyl-amide a) Biphenyl-2-carboxylic acid 3,5-bis-trifluoromethyl-benzylamide To a solution of 0.79 g (4 mmol) biphenyl-2-carboxylic acid in 30 ml CH$_2$Cl$_2$, 1.12 ml (8 mmol) triethylamin, 0.60 g (4 mmol) 1-hydroxy-benzotriazol and 0.76 g (4 mmol) N-(3-dimethylaminopropyl)-N'-ethylcarbodiimide hydrochloride 1.167 g (4 mmol) 3,5-bis-trifluormethyl-benzylamin was added. The reaction mixture was stirred for 16 hrs. The reaction mixture was diluted with 20 ml CH$_2$Cl$_2$, washed with 50 ml 0.5N HCl and 50 ml H$_2$O. The aqueous layers were backextracted with 50 ml CH$_2$Cl$_2$. The combined organic layers were dried (MgSO$_4$), filtered and evaporated. The residue was purified by chromatography (SiO$_2$, CH$_2$Cl$_2$/MeOH 40:1) to give 0.93 g (73%) biphenyl-2-carboxylic acid 3,5-bis-trifluoromethyl-benzylamide as a colorless solid, m.p. 86–87°.

b) Biphenyl-2-carboxylic acid (3,5-bis-trifluoromethyl-benzyl)-methyl-amide

To a solution of 0.63 g (1.50 mmol) biphenyl-2-carboxylic acid 3,5-bis-trifluoromethyl-benzylamide in 10 ml N,N-dimethylformamide 0.08 g (1.98 mmol) sodiumhydride (60% dispersion in mineral oil) was added and the reaction mixture was stirred for 1 hr. After the addition of 0.15 ml (2.4 mmol) methyl iodide at 0°, the reaction mixture was stirred for 3 hrs. at RT. The reaction mixture was distributed between 50 ml H$_2$O, 50 ml brine and 50 ml CH$_2$Cl$_2$. The phases were separated, the aqueous layer washed twice with 50 ml CH$_2$Cl$_2$. The combined organic layers were dried (MgSO$_4$), filtered and evaporated. The residue was purified by chromatography (SiO$_2$, ethyl acetate/CH$_2$Cl$_2$ 15:1) to give 0.50 g (76%) biphenyl-2-carboxylic acid (3,5-bis-trifluoromethyl-benzyl)-methyl-amide as colorless solid, m.p. 97–88°.

EXAMPLE 2

Biphenyl-2-carboxylic acid (3,5-dichloro-benzyl)-methyl-amide

In an analogous manner to that described in Example 1 a) there was obtained from biphenyl-2-carboxylic acid and 3,5-dichlorobenzylamine biphenyl-2-carboxylic acid 3,5-dichloro-benzylamide as a colorless solid, m.p. 152–153°, which was methylated as described in Example 1 b) to give biphenyl-2-carboxylic acid (3,5-dichloro-benzyl)-methyl-amide as a colorless solid, m.p 126–128°.

EXAMPLE 3

Biphenyl-2-carboxylic acid methyl-(3-methyl-5-trifluoromethyl-benzyl)-amide

In an analogous manner to that described in Example 1 a) there was obtained from biphenyl-2-carboxylic acid and 3-methyl-5-trifluoromethyl-benzylamine biphenyl-2-carboxylic acid 3-methyl-5-trifluoromethyl-benzylamide as a colorless solid, m.p. 126.7–127.1°, which was methylated as described in Example 1 b) to give biphenyl-2-carboxylic acid methyl-(3-methyl-5-trifluoromethyl-benzyl)-amide as a colorless oil, MS (EI): 383 (M$^+$).

EXAMPLE 4

2'-Bromo-biphenyl-2-carboxylic acid 3,5-bis-trifluoromethyl-benzylamide

In an analogous manner to that described in Example 1 a) there was obtained from 2'-bromo-biphenyl-2-carboxylic acid and 3,5-bis-trifluormethyl-benzylamin 2'-bromo-biphenyl-2-carboxylic acid 3,5-bis-trifluoromethyl-benzylamide as a colorless solid, MS (EI): 502 (M$^+$).

EXAMPLE 5

2'-Bromo-biphenyl-2-carboxylic acid 3,5-dichloro-benzylamide

In an analogous manner to that described in Example 1 a) there was obtained from 2'-bromo-biphenyl-2-carboxylic acid and 3,5-dichlorobenzylamine 2'-bromo-biphenyl-2-carboxylic acid 3,5-dichloro-benzylamide as a colorless solid, m.p. 122.5–123.2°.

EXAMPLE 6

2'-Bromo-biphenyl-2-carboxylic acid (3,5-bis-trifluoromethyl-benzyl)-methyl-amide In an analogous manner to that described in Example 1 a) there was obtained from 2'-bromo-biphenyl-2-carboxylic acid and (3,5-bis-trifluoromethyl-benzyl)-methyl-amine 2'-bromo-biphenyl-2-carboxylic acid (3,5-bis-trifluoromethyl-benzyl)-methyl-amide as a colorless solid, MS (EI): 514 (M–H$^+$).

EXAMPLE 7

N-(3,5-Bis-trifluoromethyl-benzyl)-N-methyl-2-naphthalen-1-yl-benzamide

In an analogous manner to that described in Example 1 a) there was obtained from 2-naphthalen-1-yl-benzoic acid and (3,5-Bis-trifluoromethyl-benzyl)-methyl-amine N-(3,5-bis-trifluoromethyl-benzyl)-N-methyl-2-naphthalen-1-yl-benzamide as a colorless solid, MS (EI): 514 (M–H$^+$).

EXAMPLE 8

2'-Methoxy-biphenyl-2-carboxylic acid (3,5-bis-trifluoromethyl-benzyl)-methyl-amide In an analogous manner to that described in Example 1 a) there was obtained from 2'-methoxy-biphenyl-2-carboxylic acid and (3,5-bis-trifluoromethyl-benzyl)-methyl-amine 2'-methoxy-biphenyl-2-carboxylic acid (3,5-bis-trifluoromethyl-benzyl)-methyl-amide as a colorless oil, MS (ISP): 468.2 (M+H)$^+$.

EXAMPLE 9

2'-Methoxy-biphenyl-2-carboxylic acid (3,5-bis-trifluoromethyl-benzyl)-methyl-amide In an analogous manner to that described in Example 1 a) there was obtained from 3'-methoxy-biphenyl-2-carboxylic acid and (3,5-bis-trifluoromethyl-benzyl)-methyl-amine 3'-methoxy-biphenyl-2-carboxylic acid (3,5-bis-trifluoromethyl-benzyl)-methyl-amide as a colorless oil, MS (ISP): 468.1 (M+H)$^+$.

EXAMPLE 10

2'-Methyl-biphenyl-2-carboxylic acid (3,5-bis-trifluoromethyl-benzyl)-methyl-amide In an analogous manner to that described in Example 1 a) there was obtained from 2'-methyl-biphenyl-2-carboxylic acid and (3,5-bis-trifluoromethyl-benzyl)-methyl-amine 2'-methyl-biphenyl-2-carboxylic acid (3,5-bis-trifluoromethyl-benzyl)-methyl-amide as a colorless oil, MS (EI): 450 (M–H)$^+$.

EXAMPLE 11

2-(3,5-Bis-trifluoromethyl-benzyloxymethyl)-biphenyl

To a solution of 1.53 g (6.26 mmol)(3,5-bis-trifluoromethyl-phenyl)-methanol in 15 ml N,N-dimethylformamide 0.30 g (7.52 mmol) sodiumhydride (60% dispersion in mineral oil) was added and the reaction mixture was stirred for 1 hr. After the addition of 1.27 g (6.26 mmol) 2-chloromethyl-biphenyl in 5 ml N,N-dimethylformamide at 0°, the reaction mixture was stirred for 3 hrs. at RT. The reaction mixture was distributed between 50 ml H$_2$O, 50 ml brine and 50 ml CH$_2$Cl$_2$. The phases were separated, the aqueous layer washed twice with 50 ml CH$_2$Cl$_2$. The combined organic layers were dried (MgSO$_4$), filtered and evaporated. The residue was purified by chromatography (SiO$_2$, hexane/ethyl acetate 40:1) to give 1.25 g (47%) 2-(3,5-bis-trifluoromethyl-benzyloxymethyl)-biphenyl as a colorless oil, MS (EI): 410 (M$^+$).

EXAMPLE 12

(3,5-Bis-trifluoromethyl-benzyl)-(2'-methoxy-biphenyl-2-ylmethyl)-amine

To a solution of 0.55 g (2.3 mmol) 3,5-bis-trifluormethylbenzaldehyde in 15 ml methanol 0.50 g (2.34 mmol)(2'-methoxy-biphenyl-2-yl)-methylamine was added and the reaction mixture was stirred for 1 hr. After addition of 0.13 g (3.45 mmol) $NaBH_4$ the reaction mixture was stirred for 1 hr and then poured into ice/water. The aqueous phase was extracted three times with 60 ml $CH_2Cl_2$. The combined organic layers were dried ($Na_2SO_4$), filtered and evaporated. The residue was purified by chromatography ($SiO_2$, $CH_2Cl_2$) to give 0.82 g (81%) (3,5-bis-trifluoromethyl-benzyl)-(2'-methoxy-biphenyl-2-ylmethyl)-amine as a colorless oil, MS (ISP): 440.3 $(M+H)^+$.

EXAMPLE 13

(3,5-Bis-trifluoromethyl-benzyl)-(2'-methoxy-biphenyl-2-ylmethyl)-methyl-amine

To a solution of 0.40 g (0.91 mmol) (3,5-bis-trifuoromethyl-benzyl)-(2'-methoxy-biphenyl-2-ylmethyl)-amine in 5 ml acetonitril and 0.35 ml (4.55 mmol) formalin (36% in water) 0.091 g (1.46 mmol) sodiumcyanoborohydride was added in small portions. The reaction mixture was stirred for 45 min and than poured into water. The aqueous phase was extracted three times with 60 ml $CH_2Cl_2$. The combined organic layers were dried ($Na_2SO_4$), filtered and evaporated. The residue was purified by chromatography ($SiO_2$, $CH_2Cl_2$) to give 0.33 g (80%) (3,5-bis-trifluoromethyl-benzyl)-(2'-methoxy-biphenyl-2-ylmethyl)-methyl-amine as a colorless oil, MS (ISP): 454.4 $(M+H)^+$.

EXAMPLE 14

N-Biphenyl-2-yl-2-(3,5-bis-trifluoromethyl-phenyl)-N-methyl-acetamide

To a solution of 272 mg (1.0 mmol) 3,5-bis(trifluoromethyl)phenylacetic acid in 1 ml tetrahydrofuran 162 mg (1.0 mmol) 1,1'-carbonyldiimidazole was added in one portion at 0°. The reaction mixture was stirred for 2 hrs at room temperature and 147 mg (0.8 mmol) biphenyl-2-yl-methyl-amine was added. Stirring was continued for 3 days at room temperature. The reaction mixture was evaporated and the residue was purified by chromatography ($SiO_2$, hexane/ethyl acetate 3:1) to give 160 mg (46%) N-biphenyl-2-yl-2-(3,5-bis-trifluoromethyl-phenyl)-N-methyl-acetamide as white crystals, MS (ISP): 438.2 $(M+H)^+$.

EXAMPLE 15

(R,S)-N-Biphenyl-2-yl-2-(3,5-bis-trifluoromethyl-phenyl)-N-methyl-propionamide a) N-Biphenyl-2-yl-2-(3,5-bis-trifluoromethyl-phenyl)-acetamide In an analogogous manner to that described in Example 14 there was obtained from 2-aminobiphenyl and 3,5-bis(trifluoromethyl)phenylacetic acid N-biphenyl-2-yl-2-(3,5-bis-trifluoromethyl-phenyl)-acetamide as white crystals, MS (ISP): 424.2 $(M+H)^+$.

b) (R.S) N-Biphenyl-2-yl-2-(3,5-bis-trifluoromethyl-phenyl)-N-methyl-propionamide To a solution of 288 mg (0.68 mmol) N-biphenyl-2-yl-2-(3,5-bis-trifluoromethyl-phenyl)-acetamide in 0.5 ml N,N-dimethylformamide under argon 204 mg (1.02 mmol) potassium hexamethyldisilazide was added at 0°. Stirring was continued for 1 h at room temperature and the reaction mixture was cooled to 0° again. At this temperature, 160 mg (1.07 mmol) methyl iodide was added. After stirring for 3 hrs. at room temperature, ethyl acetate was added and the organic layer was washed with brine, dried ($MgSO_4$) and evaporated. The residue was purified by chromatography ($SiO_2$, hexane/ethyl acetate 4:1) to give 200 mg (65%) of N-biphenyl-2-yl-2-(3,5-bis-trifluoromethyl-phenyl)-N-methyl-propionamide as white crystals, MS (ISP): 452.2 $(M+H)^+$.

EXAMPLE 16

2-(3,5-Bis-trifluoromethyl-phenyl)-N-(2'-methyl-4-nitro-biphenyl-2-yl)-isobutyramide a) 2'-Methyl1-4-nitro-biphenyl-2-ylamine A mixture of 1.0 g (4.6 mmol) 2-bromo-5-nitroaniline, 20 ml benzene, 10 ml 2 N sodium carbonate solution, 159 mg (0.14 mmol) tetrakis(triphenylphosphine)- palladium(0) and 725 mg (5.07 mmol) o-tolylboronic acid was heated under argon at 60° for 20 hrs. After cooling to room temperature, the aqueous phase was separated and washed twice with toluene. The combined organic layers were washed with brine, dried ($Na_2SO_4$) and evaporated. The residue was purified by chromatography ($SiO_2$, $CH_2Cl_2$/hexane 2:1),to yield 950 mg (91%) of 2'-methyl-4-nitro-biphenyl-2-ylamine as a pale yellow oil, MS (EI): 228 (M+).

b) 2-(3,5-Bis-trifluoromethyl-phenyl)-N-(2'-methyl-4-nitro-biphenyl-2-yl)-isobutyramide A solution of 925 mg (4.05 mmol) 2'-methyl-4-nitro-biphenyl-2-ylamine and 1.03 ml (6.08 mmol) N-ethyldiisopropylamine in 9 ml $CH_2Cl_2$ was cooled in an ice bath and a solution of 1.42 g (4.46 mmol) 2-(3,5-bis-trifluoromethyl-phenyl)-2-methyl-propionyl chloride in 1 ml $CH_2Cl_2$ was added dropwise. The reaction mixture was kept at room temperature for 2 hrs. After addition of $CH_2Cl_2$, the organic layer washed with 1 N NaOH solution and 1 N HCl solution, dried ($MgSO_4$) and evaporated to give 1.84 g (89%) 2-(3,5-bis-trifluoromethyl-phenyl)-N-(2'-methyl-4-nitro-biphenyl-2-yl)-isobutyramide as yellow crystals, MS (ISP): 511.3 $(M+H)^+$.

EXAMPLE 17

2-(3,5-Bis-trifluoromethyl-phenyl)-N-methyl-N-(2'-methyl-4-nitro-biphenyl-2-yl)-isobutyramide To a solution of 1.75 g (3.43 mmol) 2-(3,5-bis-trifluoromethyl-phenyl)-N-(2'-methyl-4-nitro-biphenyl-2-yl)-isobutyramide in 11 ml N,N-dimethylformamide under argon 4.1 ml (4.1 mmol) of 1 M potassium hexamethyldisilazide solution in tetrahydrofuran were added dropwise at 0°. Stirring was continued for 1 h at room temperature and the reaction mixture was cooled to 0° again. At this temperature 0.32 ml (5.14 mmol) methyl iodide were added. After stirring for 3 hrs at room temperature, ethyl acetate was added and the organic layer was washed with brine, dried ($MgSO_4$) and evaporated. The residue was purified by chromatography ($SiO_2$, ethyl acetate/hexane 1:1) to give 1.0 g (56%) 2-(3,5-bis-trifluoromethyl-phenyl)-N-methyl-N-(2'-methyl-4-nitro-biphenyl-2-yl)-isobutyramide as yellow crystals, MS (EI): 524 $(M^+)$.

EXAMPLE 18

N-(4-Amino-2'-methyl-biphenyl-2-yl)-2-(3,5-bis-trifluoromethyl-phenyl)-N-methyl-isobutyramide To a solution of 950 mg (1.81 mmol) 2-(3,5-bis-trifluoromethyl-phenyl)-N-methyl-N-(2'-methyl-4-nitro-biphenyl-2-yl)-isobutyramide in 12 ml tetrahydrofuran and 3 ml water 608 mg (10.87 mmol) iron powder and 3 drops trifluoroacetic acid were added. After heating at 85° for 3 hrs., the reaction mixture was cooled to room temperature and evaporated. The residue was purified by chromatography (SiO$_2$, hexane/ethyl acetate 1:4) to give 890 mg (99%) N-(4-amino-2'-methyl-biphenyl-2-yl)-2-(3,5-bis-trifluoromethyl-phenyl)-N-methyl-isobutyramide as pale yellow crystals, MS (ISP): 495.2 (M+H)$^+$.

EXAMPLE 19

2-(3,5-Bis-trifluoromethyl-phenyl)-N-(4-dimethylamino-2'-methyl-biphenyl-2-yl)-N-methyl-isobutyramide To a solution of 300 mg (0.61 mmol) N-(4-amino-2'-methyl-biphenyl-2-yl)-2-(3,5-bis-trifluoromethyl-phenyl)-N-methyl-isobutyramide in 3 ml acetone 420 mg (3.03 mmol) K$_2$CO$_3$ and 0.057 ml (0.91 mmol) methyl iodide were added. Stirring was continued overnight at room temperature. The reaction mixture was filtered and the filtrate evaporated. The residue was purified by chromatography (SiO$_2$, hexane/ethyl acetate 1:4) to give 96 mg (30%) 2-(3,5-bis-trifluoromethyl-phenyl)-N-(4-dimethylamino-2'-methyl-biphenyl-2-yl)-N-methyl-isobutyramide as a pale yellow oil, MS (ISP): 532.2 (M+H)$^+$.

EXAMPLE 20

2-(3,5-Bis-trifluoromethyl-phenyl)-N-methyl-N-(2'-methyl-4-methylamino-biphenyl-2-yl)-isobutyramide The title compound was isolated as a yellow oil, MS (ISP): 509.1 (M+H)$^+$, (44 mg, 14%) during the purification of 2-(3,5-bis-trifluoromethyl-phenyl)-N-(4-dimethylamino-2'-methyl-biphenyl-2-yl)-N-methyl-isobutyramide.

EXAMPLE 21

2-(3,5-Bis-trifluoromethyl-phenyl)-N-(2'-methoxy-biphenyl-2-yl)-N-methyl-isobutyramide A solution of 53 mg (0.25 mmol) (2'-methoxy-biphenyl-2-yl)-methyl-amine and 0.064 ml (0.375 mmol) N-ethyldiisopropylamine in 4 ml CH$_2$Cl$_2$ was cooled in an ice bath and a solution of 88 mg (0.275 mmol) 2-(3,5-bis-trifluoromethyl-phenyl)-2-methyl-propionyl chloride in 1 ml CH$_2$Cl$_2$ was added dropwise. The reaction mixture was stirred overnight at room temperature. Ethyl acetate was added and the organic layer was washed with saturated Na$_2$CO$_3$ solution, 1 N HCl solution, dried (MgSO$_4$) and evaporated. The residue was purified by chromatography (SiO$_2$, hexane/ethyl acetate 4:1) to give 107 mg (87%) 2-(3,5-bis-trifluoromethyl-phenyl)-N-(2'-methoxy-biphenyl-2-yl)-N-methyl-isobutyramide as orange crystals, MS (ISP): 496.1 (M+H)$^+$.

EXAMPLE 22

2-(3,5-Bis-trifluoromethyl-phenyl)-N-methyl-N-(2'-methyl-biphenyl-2-yl)-isobutyramide In an analogous manner to that described in Example 21 there was obtained from (2'-methyl-biphenyl-2-yl)-methyl-amine and 2-(3,5-bis-trifluoromethyl-phenyl)-2-methyl-propionyl chloride 2-(3,5-bis-trifluoromethyl-phenyl)-N-methyl-N-(2'-methyl-biphenyl-2-yl)-isobutyramide as white crystals, MS (ISP): 480.2 (M+H)$^+$.

EXAMPLE 23

2-(3,5-Bis-trifluoromethyl-phenyl)-N-(2'-chloro-biphenyl-2-yl)-N-methyl-isobutyramide In an analogous manner to that described in Example 21 there was obtained from (2'-chloro-biphenyl-2-yl)-methyl-amine and 2-(3,5-bis-trifluoromethyl-phenyl)-2-methyl-propionyl chloride 2-(3,5-Bis-trifluoromethyl-phenyl)-N-(2'-chloro-biphenyl-2-yl)-N-methyl-isobutyramide as white crystals, MS (ISP): 502.2 (M+H)$^+$.

EXAMPLE 24

N-(2'-Amino-biphenyl-2-yl)-2-(3,5-bis-trifluoromethyl-phenyl)-isobutyramide

In an analogous manner to that described in Example 16 there was obtained from 2,2'-diaminobiphenyl and 2-(3,5-bis-trifluoromethyl-phenyl)-2-methyl-propionyl chloride N-(2'-Amino-biphenyl-2-yl)-2-(3,5-bis-trifluoromethyl-phenyl)-isobutyramide as white crystals, MS (ISP): 467.2 (M+H)$^+$.

EXAMPLE 25

N-(2'-Amino-biphenyl-2-yl)-2-(3,5-bis-trifluoromethyl-phenyl)-N-methyl-isobutyramide To a solution of 151 mg (0.32 mmol) N-(2'-amino-biphenyl-2-yl)-2-(3,5-bis-trifluoromethyl-phenyl)-isobutyramide in 1 ml N,N-dimethylformamide under argon 130 mg (0.65 mmol) potassium hexamethyldisilazide were added at 0°. Stirring was continued for 1 h at room temperature and the reaction mixture was cooled to 0° again. At this temperature, 115 mg (0.81 mmol) methyl iodide were added. After stirring for 3 hrs at room temperature, ethyl acetate was added and the organic layer was washed with brine, dried (MgSO$_4$) and evaporated. The residue was purified by chromatography (SiO$_2$, ethyl acetate/CH$_2$Cl$_2$ 1:1) to give 56 mg (36%) N-(2'-amino-biphenyl-2-yl)-2-(3, 5-bis-trifluoromethyl-phenyl)-N-methyl-isobutyramide as colorless oil, MS (ISP): 481.1 (M+H)$^+$.

EXAMPLE 26

2-(3,5-Bis-trifluoromethyl-phenyl)-N-(2'-dimethylamino-biphenyl-2-yl)-isobutyramide The title compound was isolated as white crystals, MS (ISP): 495.2 (M+H)$^+$,(14 mg, 9%) during the purification of N-(2'-amino-biphenyl-2-yl)-2-(3,5-bis-trifluoromethyl-l-phenyl)-N-methyl-isobutyramide.

EXAMPLE 27

2'-Methyl-5-(4-methyl-piperazin-1-yl)-biphenyl-2-carboxylic acid (3,5-bis-trifluoromethyl-benzyl)-methyl-amide a) 2-Chloro-4-fluoro-N-methyl-benzamid To 1.00 g (5.73 mmol) of 2-chloro-4-fluorobenzoic acid were added 4.16 ml (57.3 mmol) thionyl chloride and 3 drops of DMF at 0°. After heating the mixture at reflux over night excess thionyl chloride was removed by distillation. The oily brown residue was dissolved in 5 ml CH$_2$Cl$_2$. The solution was treated with methyl amine gas at 0° C. until no exothermic reaction was observed any longer. The resulting suspension was diluted with 20 ml CH$_2$Cl$_2$/H$_2$O. The layers were separated and the aqueous layer extracted with 3 10-ml portions of CH$_2$Cl$_2$. Drying of the organic layer (Na$_2$SO$_4$) and evaporation gave 1.07 g (99.6%) 2-chloro-4-fluoro-N-methyl-benzamide as a light yellow solid. MS (EI): 187 (M$^+$).

b) 2-Chloro-N-methyl-4-(4-methyl-piperazin-1-yl)-benzamide

A mixture of 316 mg (1.68 mmol) 2-chloro-4-fluoro-N-methyl-benzamide and 0.94 ml (8.4 mmol) 1-methylpiperazine was heated at 140° for 7 h in a sealed glass tube. After cooling to room temperature excess 1-methylpiperazine was removed by distillation at 50°/0.5 mbar. The residue was partitioned between 25 ml $CH_2Cl_2$/2 N NaOH solution. The layers were separated and the aqueous layer was extracted with 3 15-ml portions of dichloromethane. The combined organic extracts were dried ($Na_2SO_4$) and evaporated. Chromatography ($SiO_2$, $CH_2Cl_2$/methanol 19:1) yielded 236 mg (52%) 2-Chloro-N-methyl-4-(4-methyl-piperazin-1-yl)-benzamide as a light yellow solid, MS (EI): 267 ($M^+$).

c) 2'-Methyl-5-(4-methyl-piperazin-1-yl)-biphenyl-2-carboxylic acid methylamide

To a solution of 125 mg (0.467 mmol) 2-chloro-N-methyl-4-(4-methyl-piperazin-1-yl)-benzamide and 0.22 ml (1.5 mmol) N,N,N',N'-tetramethylethylenediamine in 2 ml THF a solution of o-tolyllithium, prepared by addition of 2.5 ml (3.8 mmol) of a 1.5 M solution of tert.-butyllithium in pentane to a solution of 0.23 ml (1.9 mmol) 2-bromotoluene in 2 ml diethyl ether at −78°, was added dropwise at −78°. The reaction mixture was allowed to warm to −25° C. over a period of 2 h. After quenching with 1 ml water at −25° the mixture was warmed to room temperature followed by dilution with 10 ml ethyl acetate and washing with 10 ml 1 N NaOH solution. The layers were separated and the aqueous layer was extracted with 2 10-ml portions of ethyl acetate. The combined organic layers were dried ($Na_2SO_4$) and evaporated. Chromatography ($SiO_2$, $CH_2Cl_2$/methanol 19:1) afforded 55 mg (36%) 2'-Methyl-5-(4-methyl-piperazin-1-yl)-biphenyl-2-carboxylic acid methylamide as a colorless oil MS 5 (EI): 324 ($M^+$).

d) 2'-Methyl-5-(4-methyl-piperazin-1-yl)-biphenyl-2-carboxylic acid (3,5-bis-trifluoromethyl-benzyl)-methyl-amide To a solution of 50 mg (0.15 mmol) 2'-methyl-5-(4-methyl-piperazin-1-yl)-biphenyl-2-carboxylic acid methylamide in 2 ml THF 0.2 ml of a 1 M solution (0.2 mmol) of potassium hexamethyldisilazide in THF was added at 0°. After 20 min. 0.028 ml (0.15 mmol) 3,5-bis(trifluoromethyl) benzyl bromide was added dropwise to the resulting suspension. The reaction was quenched with water after 1.5 h. The mixture was diluted with 5 ml 2 N NaOH solution and extracted with 3 5-ml portions of ethyl acetate. The combined organic extracts were dried ($Na_2SO_4$) and evaporated. Chromatography ($SiO_2$, $CH_2Cl_2$/methanol 19:1) gave 25 mg (29%) 2'-Methyl-5-(4-methyl-piperazin-1-yl)-biphenyl-2-carboxylic acid (3,5-bis-trifluoromethyl-benzyl)-methyl-amide, MS (ISP): 550.5 $(M+H)^+$.

EXAMPLE 28

2'-Chloro-5-(4-methyl-piperazin-1-yl)-biphenyl-2-carboxylic acid (3,5-bis-trifluoromethyl-benzyl)-methyl-amide 2'-Chloro-5-(4-methyl-piperazin-1-yl)-biphenyl-2-carboxylic acid (3,5-bis-trifluoromethyl-benzyl)-methyl-amide (MS (570, $M+H)^+$) was prepared analogously to the preparation of 2'-methyl-5-(4-methyl-piperazin-1-yl)-biphenyl-2-carboxylic acid (3,5-bis-trifluoromethyl-benzyl)-methyl-amide (Example 27) using 2-bromochlorobenzene instead of o-bromotoluene in step c).

EXAMPLE 29

4'-Fluoro-2'-methyl-biphenyl-2-carboxylic acid (3,5-bis-trifluoromethyl-benzyl)-methyl-amide In an analogous manner to that described in Example 1a) there was obtained from 4'-fluoro-2'-methyl-biphenyl-2-carboxylic acid and (3,5-bis-trifluormethyl)-methyl- benzylamine 4'-fluoro-2'-methyl-biphenyl-2-carboxylic acid (3,5-bis-trifluoromethyl-benzyl)-methyl-amide as a colorless oil, MS (EI): 468 $(M–H)^+$.

The 4'-fluoro-2'-methyl-biphenyl-2-carboxylic acid used as the starting substance was obtained as follows:

a) (4'-Fluoro-2'-methyl-biphenyl-2-ylmethylene)-isopropyl-amine

A solution of 14.57 g (81 mmol) N-(2-methoxybenzylidene)isopropylamin in 50 ml THF was added dropwise to a Grignard reagent prepared from 18.01 g (90 mmol) 2-bromo-5-fluorotoluene and 2.19 g (90 mmol) magnesium turnings in 50 ml THF. The mixture was heated at reflux for 12 hrs. The mixture was poured with vigorous stirring into an aqueous solution of $NH_4Cl$ (25 %) and stirred for 1 h. Extraction with $CH_2Cl_2$, drying ($Na_2SO_4$) and evaporation gave 20.83 g (98%) (4'-fluoro-2'-methyl-biphenyl-2-ylmethylene)-isopropyl-amine as a pale yellow oil.

b) 4'-Fluoro-2'-methyl-biphenyl-2-carbaldehyde

A solution of 20.36 g (79.8 mmol) (4'-fluoro-2'-methyl-biphenyl-2-ylmethylene)-isopropyl-amine in 110 ml 4N $H_2SO_4$ was heated at reflux for 6 h. After cooling to RT, the solution was extracted twice with 150 ml $CH_2Cl_2$. The combined organic layers were dried ($Na_2SO_4$), filtered and evaporated. The residue was purified by chromatography ($SiO_2$, $CH_2Cl_2$/hexane 1:1) to give 4'-fluoro-2'-methyl-biphenyl-2-carbaldehyde as a pale yellow oil.

c) 4'-Fluoro-2'-methyl-biphenyl-2-carboxylic acid

To a solution of 2.70 g (12.6 mmol) 4'-fluoro-2'-methyl-biphenyl-2-carbaldehyde in 75 ml aceton and 25 ml $H_2O$ 3.38 g (21.4 mmol) $KMnO_4$ were added and the mixture stirred for 20 hrs. The solvent was evaporated, the residue treated with 100 ml $H_2O$ and 100 ml $CH_2Cl_2$ and the pH of the aqueous phase was adjusted to 1 with conc. $H_2SO_4$. After filtration through the phases were separated and the aqueous phase washed twice with 100 ml $CH_2Cl_2$. The combined organic layers were dried ($Na_2SO_4$), filtered and evaporated. The residue was purified by chromatography ($SiO_2$, $CH_2Cl_2$/MeOH 19:1) to give 4'-fluoro-2'-methyl-biphenyl-oxylic acid as a colorless solid, MS (EI): 230, ($M^+$).

Table 1 sets for the subtituents for each compound of the previously described Examples.

TABLE 1

| Example No. | R | R¹ n = 1 | R² n = 2 | R³ | R⁴ | R⁵ | X |
|---|---|---|---|---|---|---|---|
| 1 | H | H | 3,5-CF₃ | H/H | H | H | −C(=O)−N(CH₃)−CH₃ |
| 2 | H | H | 3,5-Cl | H/H | H | H | −C(=O)−N(CH₃)−CH₃ |
| 3 | H | H | 3-CF₃, 5-CH₃ | H/H | H | H | −C(=O)−N(CH₃)−CH₃ |
| 4 | Br | H | 3,5-CF₃ | H/H | H | H | −C(=O)−NH−CH₃ |
| 5 | Br | H | 3,5-Cl | H/H | H | H | −C(=O)−NH−CH₃ |
| 6 | Br | H | 3,5-CF₃ | H/H | H | H | −C(=O)−N(CH₃)−CH₃ |
| 7 | are together —CH=CH—CH=CH— | | 3,5-CF₃ | H/H | H | H | −C(=O)−N(CH₃)−CH₃ |
| 8 | OCH₃ | H | 3,5-CF₃ | H/H | H | H | −C(=O)−N(CH₃)−CH₃ |
| 9 | H | m-OCH₃ | 3,5-CF₃ | H/H | H | H | −C(=O)−N(CH₃)−CH₃ |
| 10 | CH₃ | H | 3,5-CF₃ | H/H | H | H | −C(=O)−N(CH₃)−CH₃ |
| 11 | H | H | 3,5-CF₃ | H/H | H | H | CH₂—O— |
| 12 | OCH₃ | H | 3,5-CF₃ | H/H | H | H | —CH₂—NH— |
| 13 | OCH₃ | H | 3,5-CF₃ | H/H | H | H | —CH₂—N(CH₃)— |

TABLE 1-continued

| Example No. | R | R¹ n = 1 | R² n = 2 | R³ | R⁴ | R⁵ | X |
|---|---|---|---|---|---|---|---|
| 14 | H | H | 3,5-CF₃ | H/H | H | H | C(=O)N(CH₃)₂ |
| 15 | H | H | 3,5-CF₃ | CH₃/H | H | H | C(=O)N(CH₃)₂ |
| 16 | CH₃ | H | 3,5-CF₃ | CH₃/CH₃ | H | NO₂ | C(=O)NH(CH₃) |
| 17 | CH₃ | H | 3,5-CF₃ | CH₃/CH₃ | H | NO₂ | C(=O)N(CH₃)₂ |
| 18 | CH₃ | H | 3,5-CF₃ | CH₃/CH₃ | H | NH₂ | C(=O)N(CH₃)₂ |
| 19 | CH₃ | H | 3,5-CF₃ | CH₃/CH₃ | H | N(CH₃)₂ | C(=O)N(CH₃)₂ |
| 20 | CH₃ | H | 3,5-CF₃ | CH₃/CH₃ | H | NH(CH₃) | C(=O)N(CH₃)₂ |
| 21 | OCH₃ | H | 3,5-CF₃ | CH₃/CH₃ | H | H | C(=O)N(CH₃)₂ |
| 22 | CH₃ | H | 3,5-CF₃ | CH₃/CH₃ | H | H | C(=O)N(CH₃)₂ |
| 23 | Cl | H | 3,5-CF₃ | CH₃/CH₃ | H | H | C(=O)N(CH₃)₂ |

TABLE 1-continued

| Example No. | R | R¹ n = 1 | R² n = 2 | R³ | R⁴ | | R⁵ | X |
|---|---|---|---|---|---|---|---|---|
| 24 | NH₂ | H | 3,5-CF₃ | CH₃/CH₃ | H | | H | N-methylacetamide (NH) |
| 25 | NH₂ | H | 3,5-CF₃ | CH₃/CH₃ | H | | H | N,N-dimethylacetamide |
| 26 | N(CH₃)₂ | H | 3,5-CF₃ | CH₃/CH₃ | H | | H | N,N-dimethylacetamide |
| 27 | CH₃ | H | 3,5-CF₃ | H/H | | piperazine | H | N,N-dimethylacetamide |
| 28 | Cl | H | 3,5-CF₃ | H/H | | piperazine | H | N,N-dimethylacetamide |
| 29 | CH₃ | F | 3,5-CF₃ | H/H | H | | H | N,N-dimethylacetamide |

EXAMPLE A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository molds of suitable size, left to cool, the suppositories are then removed from the molds and packed individually in wax paper or metal foil.

What is claimed is:

1. A compound of formula:

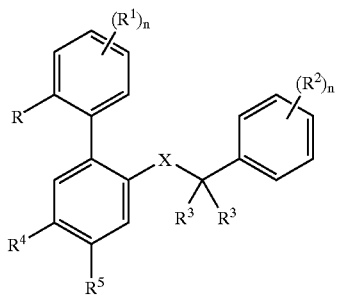

I wherein
R is hydrogen, lower alkyl, lower alkoxy, halogen, amino, —N(R$^6$)$_2$ or trifluoromethyl;
R$^1$ is hydrogen, lower alkoxy or halogen;
R and R$^1$ may be together —CH=CH—CH=CH—;
R$^2$ is halogen, lower alkyl or trifluoromethyl;
R$^3$ is hydrogen or lower alkyl;
R$^4$ is hydrogen or a cyclic tertiary amine, optionally substituted by lower alkyl;
R$^5$ is hydrogen, nitro, amino or —N(R$^6$)$_2$;
R$^6$ is hydrogen or lower alkyl;
X is —(CH$_2$)$_n$O—; and
n is 1 or 2;
or a pharmaceutically acceptable acid addition salt thereof.

2. A compound according to claim 1, wherein the compound is 2-(3,5-Bis-trifluoromethyl-benzyloxymethyl)-biphenyl.

3. A process for preparing a compound of formula I as defined in claim 1, comprising:

reacting a compound of formula:

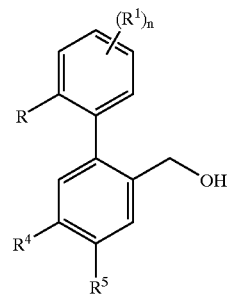

VIII with a compound of formula:

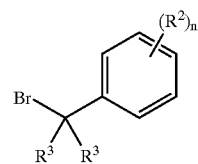

VII to yield a compound of formula:

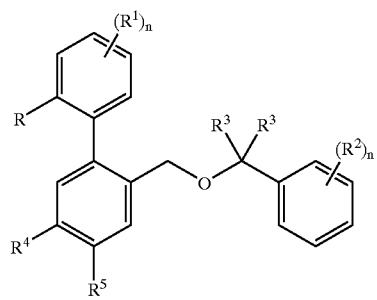

I-5 wherein the definitions of substituents are given in claim 1.

4. A process for preparing a compound of formula I as defined in claim 1, comprising:

reacting a compound of formula:

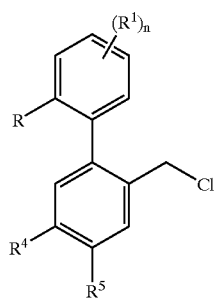
with a compound of formula:
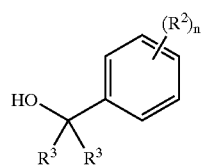
to yield a compound of formula:
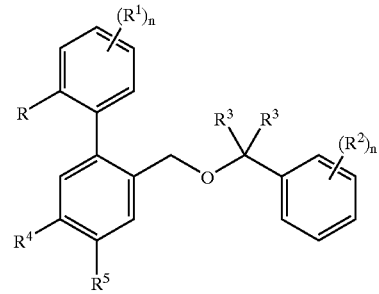
wherein the definitions of substituents are given in claim 1.
* * * * *